United States Patent [19]

Hao et al.

[11] Patent Number: 5,523,061
[45] Date of Patent: Jun. 4, 1996

[54] EQUIPMENT FOR CATALYTIC DISTILLATION

[75] Inventors: Xingren Hao; Jinshan Wang; Zongren Yang; Yuping Xing, all of Xindian; Longxing Xu; Shuxian Jiang, both of Beijing, all of China

[73] Assignee: China Petrochemical Corporation (SINOPEC), Beijing, China

[21] Appl. No.: 513,664

[22] Filed: May 31, 1995

Related U.S. Application Data

[63] Continuation of Ser. No. 820,118, Jan. 13, 1992, abandoned, which is a continuation-in-part of Ser. No. 440,132, Nov. 22, 1988, abandoned.

[30] Foreign Application Priority Data

Nov. 24, 1988 [CN] China ................................ 88109705

[51] Int. Cl.$^6$ .................................................. B01J 8/04
[52] U.S. Cl. ..................... 422/191; 422/194; 203/DIG. 6
[58] Field of Search ..................................... 422/187, 191, 422/194; 203/DIG. 6

[56] References Cited

U.S. PATENT DOCUMENTS

| Re. 23,638 | 3/1953 | Peters | 422/194 |
|---|---|---|---|
| 4,503,265 | 3/1985 | Schleppinghoff | 568/699 |
| 4,847,430 | 6/1989 | Quang et al. | 422/193 |

*Primary Examiner*—Lyle A. Alexander
*Attorney, Agent, or Firm*—Armstrong, Westerman, Hattori, McLeland & Naughton

[57] ABSTRACT

The present invention relates to catalytic distillation equipment having a reaction section divided into several beds by separating plates. New catalyst is packed into the beds through a packing inlet. Used catalyst is withdrawn from a packing outlet. The invention has the advantages of permitting greater contact between reactants and catalyst which increases the reaction rate and efficiency of catalyst.

10 Claims, 3 Drawing Sheets

EQUIPMENT FOR CATALYTIC DISTILLATION

This application is a Continuation application Ser. No. 07/820,118 filed Jan. 13, 1992, now abandoned which is a continuation-in-part application of our U.S. patent application Ser. No. 07/440,132, filed on Nov. 22, 1988, for "Equipment For Catalytic Distillation" now abandoned.

BACKGROUND OF THE INVENTION

The present invention relates to a novel kind of equipment of catalytic distillation technology in chemical industry and a new catalyst handling system for use therein. The present invention is especially useful for the production of methyl tertiary butyl ethers (MTBE) from methanol and isobutene contained in $C_4$ stream.

It is well-known that a catalytic distillation column is an apparatus for carrying out distillation and chemical reaction simultaneously therein to drive an equilibrium -limited reaction to completion by removing at least one of the products by virtue of their difference in boiling point. Because the reaction heat is absorbed by liquid evaporation, it can be fully utilized. What is more, the reaction is carried out at constant temperature without additional heat exchanger.

In order to carry out reaction and separation concurrently, and to make possible upward vapor and downward liquid flow through the reaction section in the middle of the catalytic distillation column, many structures have been developed. U.S. Pat. No. 3,634,543 discloses a reaction process carried out in distillation column wherein catalyst is contained in the downcomers of distillation trays in the column as additional bed, so that the catalytic reaction takes place in the catalyst beds and the distillation takes place on the trays in the column. The problems which arise are that the catalyst in the downcomers may cause flooding and that the loading of the catalyst is rather complicated.

U.S. Pat. No. 4,439,350 discloses a structure for holding catalyst in perforated or porous metal or plastic containers, such as fine stainless steel baskets. The containers are placed on the conventional distillation tray so that the liquid reactants would flow in and through the containers, and the vapor would be easily released from the liquid. When flowing through the trays, the reactants diffuse into the catalyst bed and react there.

In addition, U.S. Pat. No. 4,215,011 discloses a catalyst handling system wherein the particulate catalyst is contained in an array of bags made of glass fiber cloth and enclosed in stainless steel mesh. These bags are placed in the reaction section of the column. Between the bags there is a space to permit vapor and liquid to go through this section countercurrently.

All kinds of catalyst holding structures described above have the disadvantage of being relatively complicated and expensive to manufacture and replace Also, it is difficult to load new catalyst or to withdraw the used catalyst.

To carry out these operations, the operator will have to work in the column. Finally, because catalyst is packed in bags the reactants will have to diffuse into the bags to react therein, while the products must diffuse out. Therefore, the very inefficient contact of reactants with catalyst results in too poor utilization to achieve the desired chemical conversion.

SUMMARY OF THE INVENTION

The present invention relates to a novel equipment for catalytic distillation comprising three sections. The upper is a rectifying section, the middle is a reaction section and the lower is a stripping section. The reaction section comprises a plurality of catalyst beds each of which is bounded by a top wall and a bottom wall, said top wall being a perforated plate and said bottom wall being a perforated catalyst-supporting plate, at least one catalyst flow pipe disposed between each pair of adjacent catalyst beds of said plurality of catalyst beds for connecting said catalyst beds making them continuously, each of said plurality of catalyst beds has at least one vapor riser passing generally vertically therethrough, said vapor riser of each of said catalyst beds being higher than the surface of the respective catalyst bed to form a weir for preventing liquid flowing into said vapor riser and maintaining a height of a liquid layer on the surface of the respective catalyst bed for distributing the liquid uniformly across the top wall, at least one distillation tray being disposed in the space between each pair of adjacent catalyst beds of said plurality of catalyst beds, said tray having one downcomer extending therethrough and being disposed at the center of said tray, said downcomer supplying liquid to the top wall of the catalyst bed therebelow, a liquid seal trough disposed below each of said downcomer making the liquid flow uniformly into the liquid layer on the surface of said catalyst bed, a handlhole disposed at an uppermost portion of each of said plurality of catalyst beds.

For reactions with high conversion, in order to reduce the height of said catalytic distillation equipment, a pre-reactor is installed upstream. The reactants react to the predetermined conversion in the pre-reactor, then are fed into said equipment to complete the reaction. Said pre-reactor is an adiabatic fixed-bed device comprising a catalyst bed, a feed inlet disposed at an uppermost portion of said catalyst bed and a product outlet disposed at the bottom of said catalyst bed. Said catalyst bed can be divided into a plurality of catalyst bed sections connected by catalyst flow pipe. There is a sideline inlet between each two adjacent catalyst bed sections. A part of the unpreheated feedstock is fed into the pre-reactor through the sideline to regulate the temperature.

The catalyst used in the equipment for catalytic distillation of the present invention is directly packed into the catalyst beds in the reaction section without any particular packages. Like any conventional fixed-bed reactor, the catalyst is directly packed into each of said plurality of catalyst beds through the uppermost inlet and through the catalyst flow pipe disposed between each pair of adjacent catalyst beds, while the used catalyst in withdrawn from the lowermost outlet and through said catalyst flow pipe directly. This makes the catalyst handling system very simple. Because of the absence of any additional package, the reactants contact the catalyst directly instead of diffusing through the package. This promotes the reaction.

The equipment of the present invention can be used for a catalytic reversible reaction to simplify operation and to save time and man power.

DETAILED DESCRIPTION OF THE INVENTION AND PREFERRED EMBODIMENTS

The present invention will be further described in detail with the corresponding figures hereinafter.

Figure 1:
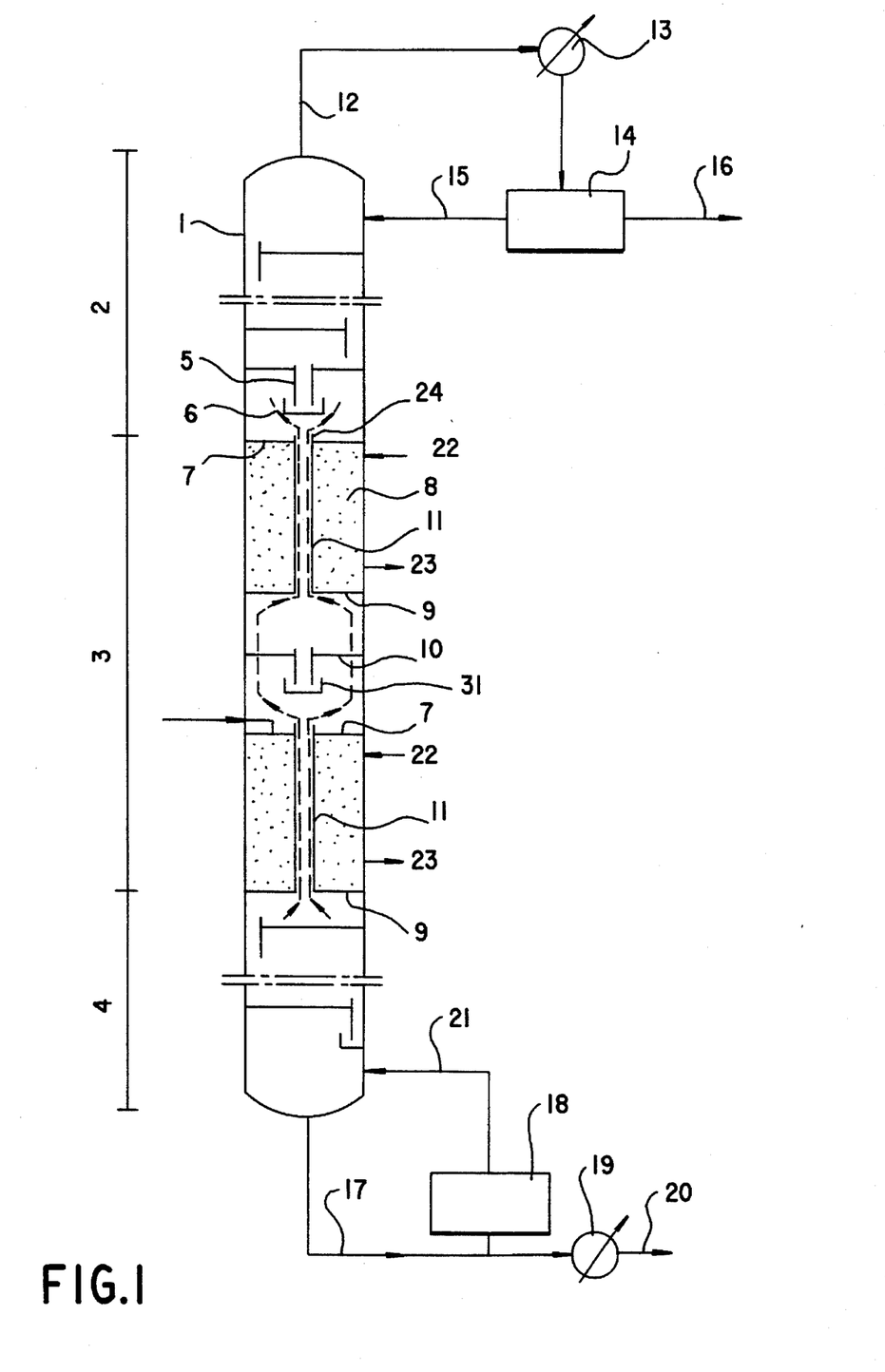
FIG. 1 is an elevational view of the equipment for catalytic distillation of the present invention.

Equipment for catalytic distillation according to a first embodiment of the present invention is shown in FIG. 1. The equipment comprises three sections. The upper is a rectifying section 2, the middle is a reaction section 3, the lower is a stripping section 4. Said reaction section 3 comprises a plurality of catalyst beds each of which is bounded by a top wall 7 and a bottom wall 9, said top wall 7 is a perforated plate, said bottom wall is a perforated catalyst-supporting plate, said plurality of catalyst beds are connected by catalyst flow pipes 25 disposed between each pair of said adjacent catalyst beds to make said plurality of catalyst beds continuously, each one of said plurality of catalyst beds has at least one vapor riser 11 generally passing through said catalyst bed vertically, between each two adjacent catalyst beds, at least one distillation trays or a packing section 10 is disposed. The number of distillation plates or the height of the packing section in rectifying section 2 and stripping section 4, the number of the catalyst beds in the reaction section 3 and the amount of catalyst packed in each of said catalyst beds are determined by the conversion rate of the reaction and the required product purity and throughput. The liquid stream flows downward from the top of the column to the last tray of the rectifying section 2. It then flows to the top wall 7 of the first catalyst bed 8 through a downcomer 5 and a liquid seal 6, and passes downward through the catalyst bed 8 by gravity. The liquid exits from a metal or nonmetal mesh placed on the perforated catalyst-supporting plate 9, and enters the distillation tray therebelow. When passing through the catalyst bed, the liquid stream reacts and releases reaction heat. The reaction is carried out at the boiling point. The reaction heat vaporizes a part of the liquid stream, resulting in a rather constant reaction temperature and a rectification. The separation of the products formed from the reactants, by virtue of the difference between their boiling points, breaks the equilibrium of the reaction and hence improves conversion. The vapor portion (in an amount related to the conversion) formed by reaction heat either flows downward with the liquid or bubbles upward to leave the bed 8. The liquid portion coming out from the bottom of the bed 8 flows downward to tray 10 therebelow, where heat-transfer and mass-transfer occurs between the liquid going down and the vapor going up from a vapor riser 11 of the bed below. The vapor riser 11 can have an round cross-sectional shape or a bow-shaped cross-sectional configuration. The vapor portion on tray 10 rises to another tray 10 through the vapor riser 11 of the bed. The liquid portion on tray 10 flows into the next bed through a downcomer and a liquid seal trough 6 to react further. In this way, reaction and separation are carried out alternatively until the desired conversion is obtained.

After being fed into the catalytic distillation column, the reactants experience several reaction-separation cycles. The products with lower b.p. go into reflux tank 14 through the rectifying section 2, the top pipe 12 and the condenser 13. Then a part of them returns to the top through pipe 15, and the rest leaves the apparatus as low b.p. products through pipe 16. The products with high b.p. go into reboiler 18, through the stripping section 4 and bottom pipe 17. The vaporized portion returns to the bottom through pipe 21, while the rest gets out of the apparatus through cooler 19 and pipe 20.

According to the equipment for catalytic distillation of the present invention as shown in FIG. 1, only one catalyst inlet 22 is disposed at an uppermost portion of the uppermost catalyst bed of said plurality of catalyst beds and only one catalyst outlet 23 disposed at the lowermost portion of the lowermost catalyst bed of said plurality of catalyst beds for loading and withdrawing catalyst, at least one catalyst flow pipe 25 is disposed between each pair of adjacent catalyst beds of said plurality of catalyst beds for connecting said plurality of catalyst beds and making them continuously. The new catalyst is fully packed in said plurality of catalyst beds through the inlet 22 on the top of said reaction section 3 and catalyst flow pipes 25 disposed between each pair of said adjacent catalyst beds, while the used catalyst is fully withdrawn from the outlet 23 on the bottom of said reaction section 3 and the flow pipe 25. A handhole 26 is disposed at the uppermost portion of each of said plurality of catalyst beds for observing and leveling the catalyst surface therein.

Preferably, at least one stainless steel or nonmetal wire meshes are installed below said top wall and on said bottom wall of each of said plurality of catalyst beds respectively.

In order to make liquid stream flow uniformly through the catalyst bed, the vapor riser passes through the catalyst bed and is higher than the surface of the catalyst bed to form a weir 24 for maintaining a certain height of liquid layer on the surface of the catalyst bed so as to make the liquid flow uniformly through the catalyst bed, the liquid flow rate through each of said plurality of catalyst beds can be regulated by the fluctuation of the liquid level automatically. Generally, the height of the weir is preferably in the range of 30 to 100 mm. The height of the liquid layer above the upper surface of the catalyst beds is maintained by choosing a suitable height of catalyst beds and operation conditions based on the hydrodynamic study.

Based on the diameter of the column and the handling type of the catalyst, at least one vapor riser 11 can be disposed either in the center or at the side of said catalyst bed.

The construction material for rectifying 2 and stripping 4 sections of said catalytic distillation column are conventional ones used in usual design, while the material for reaction section 3 can be stainless steel, alloy steel or carbon steel with lining in accordance with the requirement of corrosion-resistance.

Figure 2:
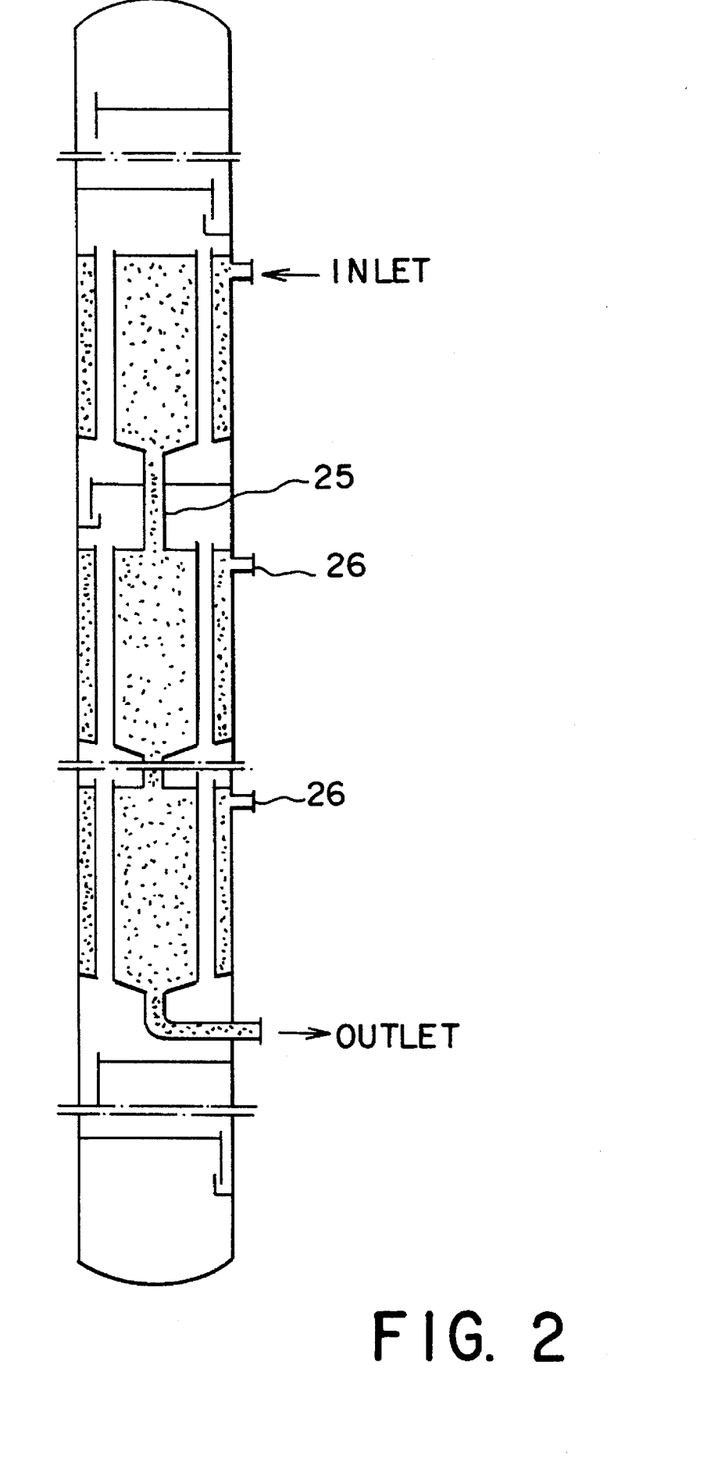
FIG. 2 is a schematic representation of a pre-reactor having catalyst flow pipes connecting adjacent catalyst beds
Figure 3:
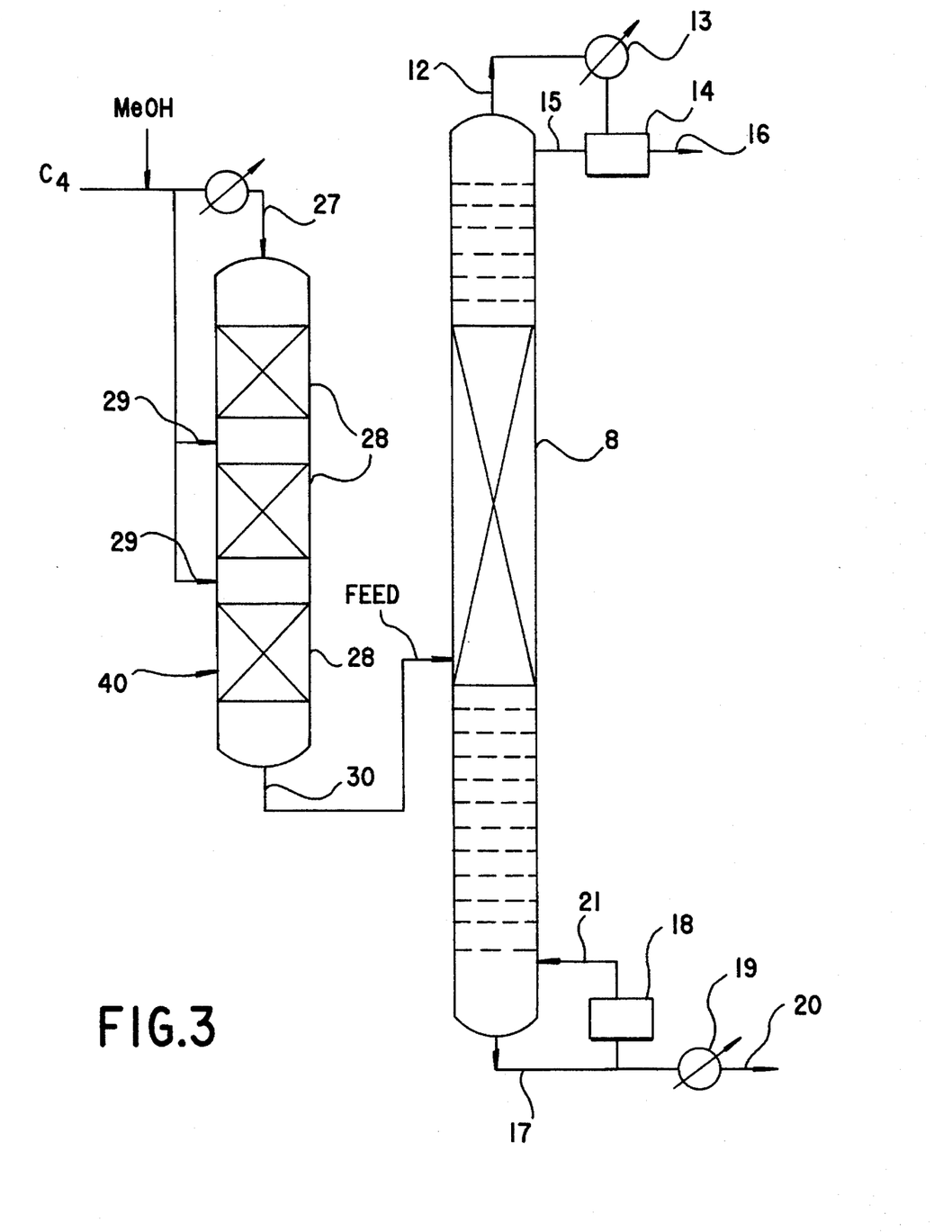
FIG. 3 is a schematic representation of the equipment for catalytic distillation combined with a pre-reactor.

With regard to deep conversion reaction, generally, the equipment for catalytic distillation thereof is high. In order to reduce its height, a pre-reactor 40, which is an adiabatic fixed-bed reactor as shown in FIG. 2, is installed upstream. The mixed feedstocks enter the top 27 of the pre-reactor 40 and pass through the catalyst beds downward. For exothermal reaction, a gas-liquid mixed regime is utilized in the pre-reactor. The reactants preheated to a temperature lower than the boiling point of the feedstocks under the operation pressure and sufficiently to initiate the reaction enter the pre-reactor reactor, react, and release heat due to the action of catalyst 28,the reaction temperature can be increased gradually by absorbing the reaction heat. When the temperature of the reactants increased to the boiling point, part of the liquid start to vaporize, and the reaction temperature will be maintained at the b.p. under this operating pressure. When the predetermined conversion is achieved, the products coming out from the bottom 30 of said pre-reactor are fed directly into said catalytic distillation column in the form of gas-liquid mixture without cooling. The mixture will continue to react in the column until the desired conversion is reached.

In pre-reactor 40, if the concentration of feedstock is low, only a single catalyst bed is utilized. If the concentration is high, the catalyst bed can be divided into two or more bed sections 28 and are connected by catalyst flow pipe 35 to prevent overheating. A part of cold feedstock can be fed through the sideline inlets 29 between each pair of adjacent beds to prevent overheating and regulate the reaction temperature.

The equipment of the present invention can be used for synthesizing MTBE from methanol and isobutene contained in a $C_4$ stream; producing esters from organic acids and alcohols; hydration of olefin; alkylation of alkyl and aromatic hydrocarbon; and other reversible reactions as well. The range of boiling point can be changed by regulating the reaction pressure so that the reaction is carried out at b.p. under that pressure.

The utility of the above-described invention is further illustrated by reference to the following examples. These examples are representative only and are not limited to the invention disclosed. Certain modifications, within the scope of these teachings, will be apparent to those skilled in the art.

EXAMPLES

In the following examples, the equipment for catalytic distillation of the present invention is used for producing MTBE from methanol and isobutene contained in $C_4$ stream. The composition of $C_4$ stream is shown as follows.

| Component | Example of the Present Invention (in wt %) | | | U.S. Pat. No. 4,336,407 4 (in mole %) |
|---|---|---|---|---|
| | 1 laboratory Column | 2,3,5,6 pilot plant column | | |
| Isobutane | 3.47 | 13.56 | 2.96 | 2.8 |
| n-Butane | 47.35 | 17.17 | 4.99 | 8.6 |
| Butene-1 | 23.75 | 35.71 | 44.41 | 24.8 |
| Isobutene | 19.60 | 20.92 | 39.13 | 50.5 |
| Trans-butene-2 | 7.03 | 11.79 | 8.50 | 3.1 |
| Cis-butene-2 | | | | 10.4 |
| Butadiene | | 0.84 | | 0.5 |
| ratio butene-1\butene-2 | | | | 1.8 |

The laboratory catalytic distillation column is a 1 inch diameter and 12 feet tall tube. The pilot plant column is 3 inches in diameter and 59 feet in height.

EXAMPLES 1–4

The reaction section of the catalytic distillation column shown in FIG. 1 is packed with S-type catalyst, which is loaded directly through the inlet 22. In rectifying and stripping sections and between the catalyst beds, there is Dixon packing, the reactants are preheated and enter the column at the lower part of the reaction section. The liquid stream flows downward from the top of the column-to the bottom of the rectifying section through packing by gravity. It then flows to the top 7 of the first catalyst bed through downcomer 5 and liquid seal trough 6, passes downwardly through the catalyst bed 8. It gets out from the stainless steel net placed on perforated catalyst-supporting plate 9 and enters the stripping section therebelow. When passing through the catalyst bed, the liquid stream containing methanol and isobutene reacts to produce MTBE and heat. The reaction is carried out at 77° to 80° C.

The reaction heat evaporates a part of the liquid stream and the vaporized stream carries away heat so as to maintain a constant reaction temperature and to act as rectification. The separation of MTBE from methanol and isobutene by virtue of the difference between their b.p. breaks the equilibrium of the reaction and increases conversion. The vapor portion formed in the catalyst bed either flows downward with liquid or bubbles upward to leave the bed. The liquid portion from the bottom of the bed 8 flows downward to the packing 10 therebelow, where it exchanges heat and mass with the vapor from the vapor riser 11 of the lower bed. The vapor portion in packing 10 rises into the rectifying section above through the vapor riser of the upper bed and further exchanges heat and mass with liquid stream. The liquid portion from packing 10 flows into the lower bed to continue reaction. Reaction and separation are alternatively carried out in such a way until the desired conversion is achieved.

After being fed into the catalytic distillation column, methanol and isobutene experience several reaction-separation cycles. A $C_4$ stream of low b.p. and a small amount of methanol go into reflux tank 14 through rectifying section 2, the top pipe 12 and condenser 13. Then some of the condensate returns to the top of the column through pipe 15, and the rest leaves the apparatus through pipe 16. The MTBE products of high b.p. go into reboiler 18 through stripping section and bottom pipe 17. The vaporized stream in the reboiler returns to the column bottom through pipe 21, while the rest leaves the apparatus through cooler 19 and pipe 20.

The reaction conditions and experimental results are shown as follows.

| | Example | | | |
|---|---|---|---|---|
| | 1 Lab column | 2 | 3 Pilot Plant Column | 4 |
| $LHSV^{-1}$* (hr) | 0.44 | 0.19 | 0.16 | 0.29 |
| System Pressure ($Kg/cm^2$) | 10 | 10.9 | 11.1 | 8.0 |
| Temperature: (°C.) | | | | |
| Overhead | 73 | 72 | 75 | 68 |
| Bottoms | 150 | 156 | 163 | 141 |
| Recovery Rate | | | | |
| Overhead | 128.21 g/hr | 13.42 L/hr | 16.44 L/hr | 11.25 L/hr |
| Bottoms | 45.24 g/hr | 3.07 L/hr | 3.75 L/hr | 9.50 L/hr |
| Methanol Feed (ml/min.) | 0.4 | 18.13 | 27.25 | 45.84 |
| Overhead (wt %) | | | | |
| Methanol | 1.98 | 3.12 | 3.21 | 3.90 |

|  | Example | | | |
|---|---|---|---|---|
|  | 1<br>Lab column | 2 | 3<br>Pilot Plant Column | 4 |
| Isobutane | 4.11 | 14.50 | 14.68 | 4.59 |
| n-butane | 55.76 | 19.28 | 19.44 | 7.75 |
| Butene-1 | 28.08 | 47.03 | 45.97 | 66.50 |
| Isobutene | 1.57 | 1.96 | 2.05 | 4.05 |
| Trans-butene-2 | 8.1 | 13.64 | 13.83 | 13.20 |
| Butadiene |  | 0.82 | 0.82 |  |
| Bottoms (wt %) |  |  |  |  |
| Methanol and $C_4$ | 1.68 | 1.0 | 1.19 | 0.28 |
| Tert-Butyl alcohol | 1.44 | 1.26 | 1.37 | 1.1 |
| Methyl tertiary butyl ether (MTBE) | 96.88 | 97.74 | 97.43 | 98.62 |
| Amount of Catalyst | 100 ml<br>(56 g) | 2572 ml<br>(1440 g) | 2572 ml<br>(1440 g) | 3215 ml<br>(1800 g) |

*$LHSV^{-1}$ is the ratio between overhead takeoff rate and the volume resin in the catalytic zone.

EXAMPLES 5–6

The following two examples relate to deep conversion more than 99% isobutene.

In example 5, the catalytic distillation column shown in FIG. 1 was used and the procedure described in examples 1–4 hereinabove was followed.

In example 6, in order to reduce the height of the said column, a pre-reactor, which is a fixed-bed reactor, was installed before the column as shown in FIG. 2. The mixed feedstocks containing $C_4$ stream and methanol enter the top 27 of the pre-reactor, react and give out heat simultaneously in the action of catalyst 28 when temperature rises to b.p. of the reactants due to reaction heat, some liquid will vaporize, which maintains the reaction temperature to the b. p. under corresponding system pressure. When the predetermined conversion of isobutene is achieved, the products containing MTBE from the bottom 30 of the pre-reactor are fed directly into the lower portion of the reaction section of said catalytic distillation column in form of gas-liquid mixture without cooling. Then the procedure described in examples 1–4 hereinabove is followed until a 99 to 99.50% or higher conversion of isobutene is achieved. By using this technology, the reaction heat in the pre-reactor is carried into the catalytic distillation column instead of being taken away by cooler, so the heat is made full of use.

The reaction conditions and experimental results are shown as follows.

|  | Example | |
|---|---|---|
|  | 5<br>Without<br>Pre-reactor | 6<br>With<br>Pre-reactor |
| $LHSV^{-1}$ (hr) | 0.47 | 0.19 |
| System pressure (Kg/cm$^2$) | 9.0 | 9.0 |
| Temperature (°C.) |  |  |
| Overhead | 76 | 75 |
| Bottoms | 147 | 148 |
| Recovery Rate (L/hr) |  |  |
| Overhead | 11.04 | 13.52 |
| Bottoms | 2.58 | 3.74 |
| Methanol Feed (ml/min.) | 21.94 | 26.37 |

|  | Example | |
|---|---|---|
|  | 5<br>Without<br>Pre-reactor | 6<br>With<br>Pre-reactor |
| Overhead (wt %) |  |  |
| Methanol | 2.68 | 2.97 |
| Isobutane | 14.33 | 14.47 |
| n-Butane | 21.06 | 20.84 |
| Butene-1 | 46.39 | 46.26 |
| Isobutene | 0.04 | 0.06 |
| Trans-butene-2 | 14.46 | 14.31 |
| Butadiene | 1.03 | 1.09 |
| Bottoms (wt %) |  |  |
| Methanol and $C_4$ | 0.21 | 0.05 |
| Tertiary Butyl alcohol | 1.29 | 1.31 |
| Methyl tertiary butyl ether (MTBE) | 98.50 | 98.64 |
| Amount of catalyst | 5144 ml<br>(2880 g) | 2572 ml<br>(1440 g)<br>(excluding pre-reaction) |

COMPARISON

In order to describe the present invention further, a comparison of the results of examples 1 and 4 with those disclosed in U.S. Pat. No. 4,336,407 is made hereinbelow.

|  | Comparison | | | |
|---|---|---|---|---|
|  | Example 1 U.S.<br>Pat. No. 4,336,407<br>Lab Column | | Example 4 U.S. Pat. No.<br>4,336,407<br>Pilot Plant Column | |
| $LHSV^{-1}$ (hr) | 0.44 | 1.0 | 0.29 | 1.4 |
| System pressure (Kg/cm$^2$) | 10 | 5.6 | 8 | 7.0 |
| Temperature (°C.) |  |  |  |  |
| Overhead | 73 | 60 | 68 | 71 |
| Bottoms | 150 | 110 | 141 | 125 |
| Recovery Rate |  |  |  |  |
| Overhead | 128.21 g/hr | 120 g/hr | 11.25 L/hr | 3.06 L/hr |
| Bottoms | 45.24 g/hr | 264 g/hr | 9.5 L/hr | 4.98 L/hr |

-continued

|  | Comparison | | | |
| --- | --- | --- | --- | --- |
|  | Example 1 U.S. Pat. No. 4,336,407 Lab Column | | Example 4 U.S. Pat. No. 4,336,407 Pilot Plant Column | |
| Methanol Feed (ml/min.) | 0.4 | 2.5 | 45.84 | 24 |
| Overhead (wt %) | | | | |
| Methanol | 1.98 | | 3.90 | |
| Isobutane | 4.11 | 6.1 | 4.59 | 6.1 |
| n-butane | 55.76 | 18 | 7.75 | 15.8 |
| Butene-1 | 28.08 | 40.6 | 66.50 | 47.10 |
| Isobutene | 1.57 | 11.2 | 4.05 | 1.3 |
| Trans-butene-2 | 8.1 | 18.8 | 13.20 | 24.2 |
| Cis-butene-2 | | 5.1 | | 5.2 |
| Butadiene | | 0.3 | | 0.3 |
| Bottoms (wt %) | | | | |
| Methanol and $C_4$'s | 1.68 | 5.5 | 0.28 | 1.3 |
| Tertiary Butyl alcohol | 1.44 | 2.5 | 1.1 | 0.7 |
| Methyl Tertiary Butyl Ether (MTBE) | 96.88 | 93.2 | 98.62 | 91.9 |
| $C_8$'s and heavier | | 0.8 | | 6.1 |
| Amount of catalyst | 100 ml (56 g) | 190 ml (115 g) | 3215 ml (1800 g) | 4400 ml (2640 g) |

What is claimed is:

1. Equipment for catalytic distillation, comprising:

a rectifying section, a reaction section, and a stripping section;

said reaction section consisting of a plurality of catalyst beds each of which is bounded by a top wall and a bottom wall, said top wall being a perforated plate and said bottom wall being a perforated catalyst-supporting plate, at least one catalyst flow pipe disposed between each pair of adjacent catalyst beds for connecting said plurality of catalyst beds to make them continuous, each of said plurality of catalyst beds having at least one vapor riser passing generally vertically therethrough, said vapor riser being higher than the surface of the catalyst bed to form a weir for preventing liquid flowing into said vapor riser and to maintain a height of liquid layer on the surface of the catalyst bed for distributing liquid uniformly across said perforated top wall, at least one distillation tray being disposed between each pair of adjacent catalyst beds, said tray having one downcomer and being disposed at the center of said tray, said downcomer supplying liquid to the top wall of the catalyst bed therebelow, a liquid seal trough disposed below each downcomer making the liquid flow uniformly to the liquid layer on the surface of said catalyst bed.

2. The equipment for catalytic distillation according to claim 1, wherein catalyst is packed in bulk in each of said plurality of catalyst beds between the respective said top wall and respective said bottom wall thereof.

3. The equipment for catalytic distillation according to claim 1, wherein one catalyst inlet is disposed at an uppermost portion of an uppermost one catalyst bed of said plurality of catalyst beds, and one catalyst outlet is disposed at a lowermost portion of a lowermost catalyst bed of said plurality of catalyst beds; wherein the fresh catalyst can be fully loaded directly into each of said plurality of catalyst beds through said catalyst inlet and said catalyst flow pipe and the used catalyst in each catalyst bed of said plurality of catalyst beds can be fully withdrawn directly through said catalyst outlet and said catalyst flow pipe.

4. The equipment for catalytic distillation according to claim 1, wherein a section of packing is loaded in the space between each pair of adjacent catalyst beds for replacing the distillation tray disposed between said adjacent catalyst beds.

5. The equipment for catalytic distillation according to claim 1, wherein said weir is approximately 30 to 100 mm high for maintaining a liquid on the surface of the catalyst bed and is positioned on top of each of said vapor riser, and the liquid flow rate passing through said catalyst bed can be regulated automatically by the fluctuation of the liquid level on the surface of said catalyst bed.

6. The equipment for catalytic distillation according to claim 1, wherein an observing hole is disposed at an uppermost portion of each of said plurality of catalyst beds for observing and to level the surface of said catalyst bed.

7. The equipment for catalytic distillation according to claim 1, wherein at least one metal wire mesh or nonmetal mesh is disposed below said top wall and on the bottom wall respectively.

8. Equipment for catalytic distillation, comprising:

a pre-reactor, which is an adiabatic fixed-bed reactor, consisting of a feed inlet disposed at the top of said pre-reactor for introducing the feedstocks which is preheated to a temperature lower than the boiling point of the feedstocks under the operational pressure and sufficiently to initiate the reaction, a catalyst packed bed for carrying out the reaction and increasing the temperature of the reactants by absorbing the reaction heat until the boiling point temperature is achieved, and a product outlet disposed at the bottom of said pre-reactor for withdrawing the reacted feedstocks; and a catalytic distillation column comprising a rectifying section, a reaction section, and a stripping section, said reaction section consisting of a plurality of catalyst beds each of which is bounded by a top wall and a bottom wall, said top wall being a perforated plate and said bottom wall being a perforated catalyst-supporting plate, at least one catalyst flow pipe disposed between each pair of adjacent catalyst beds for connecting said plurality of catalyst beds to make them continuous, each of said plurality of catalyst beds having at least one vapor riser extending therethrough, said vapor riser of each of said catalyst beds being higher than the surface of the catalyst bed to form a weir for preventing liquid flowing into said vapor riser and to maintain a height of liquid layer on the surface of the catalyst bed for distributing liquid uniformly across said top wall, at least one distillation tray being disposed between each pair of adjacent catalyst beds, said at least one distillation tray having one downcomer and being disposed at the center of said at least one distillation tray, said downcomer supplying liquid to the top wall of the catalyst bed, a liquid seal trough disposed below said downcomer making the liquid flow uniformly to the liquid layer on the surface of the catalyst bed.

9. The equipment for catalytic distillation according to claim 8, wherein each of said plurality of catalyst beds in said pre-reactor is composed of at least two catalyst beds, at least one catalyst flow pipe is disposed between two adjacent catalyst beds.

10. The equipment for catalytic distillation according to claim 9, wherein a sideline feed inlet is disposed between each pair of said adjacent catalyst beds for adding a portion of unpreheated feedstocks for adjusting reaction temperature in said catalyst beds.

* * * * *

UNITED STATES PATENT AND TRADEMARK OFFICE
CERTIFICATE OF CORRECTION

PATENT NO.:   5,523,061
DATED     :   June 4, 1996
INVENTOR(S):  HAO et al.

It is certified that errors appear in the above-identified patent and that said Letters Patent is hereby corrected as shown below:

In Fig. 1 of the drawings reference numeral "31" should be deleted and reference numeral --6-- substituted therefor, as shown on the attached copy of Fig.1

In Fig. 2 of the drawings reference numeral --24-- should be added; "INLET" should be deleted and reference numeral --22-- substituted therefor; also the term "OUTLET" should be deleted and reference numeral --23-- substituted therefor; all as shown on the attached copy of Fig. 2

In Column 2 on line 58 please delete "a pre-reactor" and insert therefor --the equipment--.

In Column 3 on line 9 to line 12 please delete "said plurality ... continuously,"; also in column 3 on line 63 please delete "1" and insert therefor --2--.

In Column 4 on line 43 please delete "2" and insert therefor --3-- ; also in column 4 on lines 65-66 please delete "35 to prevent overheating".

In Column 6 on line 10 please delete "stripping section" and insert therefor --distillation tray--.

In Column 7 on line 32 please delete "2" and insert therefor --3--.

UNITED STATES PATENT AND TRADEMARK OFFICE
CERTIFICATE OF CORRECTION

PATENT NO.: 5,523,061
DATED : June 4, 1996
INVENTOR(S): HAO et al.

It is certified that errors appear in the above-identified patent and that said Letters Patent is hereby corrected as shown below:

At Column 8 at lines 53-55; and at column 9 on lines 4-6 please delete:

| Example 1 U.S. Pat. No. 4,336,407 Lab Column | Example 4 U.S. Pat. No. 4,336,407 Pilot Plant Column |
|---|---| and substitute therefor:

| Example 1 | U.S. Pat. No. 4,336,407 | Example 4 | U.S. Pat. No. 4,336,407 |
|---|---|---|---|
| Lab Column | | Pilot Plant Column | |

Signed and Sealed this

Ninth Day of June, 1998

Attest:

BRUCE LEHMAN

Attesting Officer

Commissioner of Patents and Trademarks